United States Patent
Karakelle et al.

(10) Patent No.: US 7,060,297 B2
(45) Date of Patent: Jun. 13, 2006

(54) CARRAGEENAN VISCOELASTICS FOR OCULAR SURGERY

(75) Inventors: Mutlu Karakelle, Fort Worth, TX (US); Michael R. Brunstedt, Cleveland, OH (US)

(73) Assignee: Alcon, Inc., Hunenberg (CH)

( * ) Notice: Subject to any disclaimer, the term of this patent is extended or adjusted under 35 U.S.C. 154(b) by 281 days.

(21) Appl. No.: 10/111,520

(22) PCT Filed: Nov. 5, 2001

(86) PCT No.: PCT/US01/44145

§ 371 (c)(1),
(2), (4) Date: Apr. 24, 2002

(87) PCT Pub. No.: WO02/40056

PCT Pub. Date: May 23, 2002

(65) Prior Publication Data

US 2004/0019010 A1    Jan. 29, 2004

Related U.S. Application Data

(60) Provisional application No. 60/246,236, filed on Nov. 6, 2000.

(51) Int. Cl.
*A61K 31/74* (2006.01)
*A61K 9/14* (2006.01)

(52) U.S. Cl. .................................... 424/488; 424/78.04
(58) Field of Classification Search ................ 424/427, 424/488, 78.04
See application file for complete search history.

(56) References Cited

U.S. PATENT DOCUMENTS

| | | | |
|---|---|---|---|
| 4,328,803 A | 5/1982 | Pape | |
| 5,273,056 A | 12/1993 | McLaughlin et al. | |
| 5,403,841 A | 4/1995 | Lang et al. | |
| 5,466,461 A | 11/1995 | della Valle et al. | |
| 5,616,568 A | 4/1997 | Pouyani et al. | |
| 5,618,800 A | 4/1997 | Kabra et al. | |
| 5,652,347 A | 7/1997 | Pouyani et al. | |
| 5,792,103 A | 8/1998 | Schwartz et al. | |
| 5,811,453 A | 9/1998 | Yanni et al. | |
| 5,851,229 A * | 12/1998 | Lentz et al. | 623/23.72 |
| 5,965,152 A | 10/1999 | Galin et al. | |
| 5,972,326 A * | 10/1999 | Galin et al. | 424/78.04 |
| 6,177,544 B1 | 1/2001 | Kanai et al. | |
| 6,261,547 B1 | 7/2001 | Bawa et al. | |

FOREIGN PATENT DOCUMENTS

| | | | |
|---|---|---|---|
| EP | 0 271 131 A | | 6/1988 |
| EP | 0 424 043 B1 | | 4/1991 |
| EP | 0271131 A | * | 10/1999 |
| FR | 2 698 264 A | | 5/1994 |
| WO | WO 99/58160 | | 11/1999 |
| WO | WO 00/01733 | | 1/2000 |

OTHER PUBLICATIONS

Berson et al., "Obstruction of Aqueous Outflow by Sodium Hyaluronate in Enucleated Human Eyes," *Am. J. Ophthalmology*, 95:668 (1983).
Bulpitt and Aeschlimann "New strategy for chemical modification of hyaluronic acid: Preparation of functionalized derivatives and their use in the formation of novel biocompatible hydrogels," *Biomed. Mater. Res.*, 47:152-169 (1999).
Carlsson et al., "Thermal Gelation of Nonionic Cellulose Ethers and Ionic Surfactants in Water" *Colloids Surf.*, 47:147-65 (1990).
Danishefsky and Siskovic,"Conversion of Carboxyl Groups of Mucopolysaccharides in Amides of Amino Acid Esters," *Carbohydrate Res.*, 16:199-205 (1971).
Fry, "Postoperative intraocular pressure rises : A comparison of Healon, Amvis, and Viscoat," *J. Cataract Refractive Surgery*, 15:415 (1989).
Greaves et al., "Scintigraphic Assessment of an Ophthalmic Gelling Vehicle in Man and Rabbit," *Curr. Eye Res.*, 9:415 (1990).
Gurney et al., "The Development and Use of *In Situ* Formed Gels, Triggered by pH," *Biopharm. Ocul. Drug Delivery*, pp. 81-90 (1993).
Obstbaum, "Postoperative pressure elevation. A rational approach to its prevention and management," *J. Cataract Refractive Surgery*, 81:1 (1992).
Olivius et al., "Intraocular pressure after cataract surgery with Healon®," *Am. Intraocular Implant Soc. J.*, 11:480 (1985).
Picullel et al., "Gelling Carrageenans," Food Polysaccharides and Their Applications, Ed: Stephen, A.M., Marcel Dekker:New York, vol. 67, pp. 204-244 (1995).
Rozier et al., "Gelrite: A Novel, Ion-Activated, *In Situ* Gelling Polymer for Ophthalmic Vehicles. Effect on Bioavailability of Timolol," *Int. J. Pharm.*, 57:163 (1989).
Verschueren et al., "Evaluation of various carrageenans as ophthalmic viscolysers," *STP Pharma Sci*, 6:203-210 (1996).

* cited by examiner

Primary Examiner—Carlos A. Azpuru
(74) Attorney, Agent, or Firm—Armando Pastrana, Jr.

(57) ABSTRACT

Disclosed are carrageenan-based transitional viscoelastics that will induce little or no IOP spike when left in the eye at the close of surgery thereon. Drug delivery systems for delivering therapeutic agents during post-operative recovery stages are also disclosed.

15 Claims, 8 Drawing Sheets

US 7,060,297 B2

CARRAGEENAN VISCOELASTICS FOR OCULAR SURGERY

This application claims the benefit of Provisional Application No. 60/246,236, filed Nov. 6, 2000.

FIELD OF THE INVENTION

The present invention relates to the field of viscous and viscoelastic materials suitable for use in surgical procedures. In particular, transitional viscoelastics (having non-shear related variable viscosities) comprising carrageenans, which may be left iii situ at the close of surgery, are disclosed. Methods of using transitional viscoelastics in surgery, especially ophthalmic surgery are also disclosed.

BACKGROUND OF THE INVENTION

Viscous or viscoelastic agents used in surgery may perform a number of different functions, including without limitation maintenance and support of soft tissue, tissue manipulation, lubrication, tissue protection, and adhesion prevention. It is recognized that the differing rheological properties of these agents will necessarily impact their ability to perform these functions, and, as a result, their suitability for certain surgical procedures. See, for example, U.S. Pat. No. 5,273,056.

Cataracts are opacities of the ocular lens which generally arise in the elderly. In order to improve eyesight, the cataractous lens is surgically removed and an artificial intraocular lens is inserted in its place. During these surgical procedures, viscoelastic materials are typically injected in the anterior chamber and capsular bag to prevent collapse of the anterior chamber and to protect tissue from damage resulting from physical manipulation.

A number of viscous or viscoelastic agents (hereinafter "agents") are known for ophthalmic surgical use. For example, Viscoat® (Alcon Laboratories, Inc.) which contains sodium hyaluronate and chondroitin sulfate; Healon® and Healon® GV (Pharmacia Corp.), Amvisc® Regular and Amvisc® Plus (IOLAB), and Vitrax® (Allergan) all of which contain sodium hyaluronate; and Cellugel® (Alcon) which contains hydroxypropylmethylcellulose (HPMC) are all useful in cataract surgery. They are used by the skilled ophthalmic surgeon for several purposes: maintenance of the anterior chamber of the eye and protection of ophthalmic tissues during surgery, particularly corneal endothelial cells, and as an aid in manipulating ophthalmic tissues.

While all of the agents described above may be used during cataract surgery, each has certain recognized advantages and disadvantages. See, U.S. Pat. No. 5,273,056. Generally, however, all such agents having sufficient viscosity and pseudoplasticity to be useful in ophthalmic surgery will, if left in the eye at the close of surgery, result in a transient increase in intraocular pressure ("IOP") known as an "IOP spike." (See, Obstbaum, *Postoperative pressure elevation. A rational approach to its prevention and management*, J. Cataract Refractive Surgery 18:1 (1992).) The pressure increase has been attributed to the agent's interference with the normal outflow of aqueous humor through the trabecular meshwork and Schlemm's canal. (See, Berson et al., *Obstruction of Aqueous Outflow by Sodium Hyaluronate in Enucleated Human Eyes*, Am. J. Ophthalmology 95:668 (1983); Olivius et al., *Intraocularpressure after cataract surgery with Healon®*, Am. Intraocular Implant Soc. J. 11:480 (1985); Fry, Postoperative intraocular pressure rises: A comparison of Healon, Amvis, and Viscoat, J. Cataract Refractive Surgery 15:415 (1989).) IOP spikes, depending on their magnitude and duration, can cause significant and/or irreversible damage to susceptible ocular tissues, including, without limitation, the optic nerve.

Thus, the ease with which an agent can be removed from the surgical site, typically by aspiration, has traditionally been considered an important characteristic in the overall assessment of the agent's usefulness in cataract surgery. By removing the agent before the close of surgery, the surgeon hopes to minimize or avoid any significant IOP spike. Unfortunately, however, removal of agents which are relatively dispersive (as opposed to cohesive) or which adhere to the ocular tissue is often difficult and may cause additional trauma to the eye.

Exogenous dilution of the viscoelastic has been suggested to alleviate IOP spikes. See U.S. Pat. No. 4,328,803. Depending, however, on the particular viscoelastic and the surgical technique employed, IOP spike may still be a problem. More recently, it has been suggested that the administration of degradative agents to break down conventional viscous or viscoelastic agents in the eye can reduce or avoid the occurrence of IOP spikes. See, e.g., U.S. Pat. No. 5,792,103. Such an approach requires not only the administration of a second, enzymatic agent into the eye, the biocompatibility of which must be assured; but also means for adequately mixing the two agents in a special apparatus.

Viscoelastics have also been promoted as drug delivery devices for pharmaceutical agents which are administered when the viscoelastics are applied during surgery. For example, U.S. Pat. No. 5,811,453 (Yanni et al.) discloses viscoelastics containing anti-inflammatory compounds and methods of using these enhanced viscoelastics in cataract surgery. While this approach may ameliorate ocular inflammation resulting from surgical trauma, such an approach still possesses the significant limitation of presenting IOP spike problems, as described above. Consequently, these enhanced viscoelastics still need to be aspirated out at the close of surgery.

There is, therefore, a need for an improved means for reducing or avoiding IOP spikes associated with the use of conventional viscous or viscoelastic agents in ophthalmic surgery, especially cataract surgery. More specifically, we conceived the need for an improved viscous or viscoelastic agent having a variable or transitional viscosity such that it will, without the addition of degradation agents, become substantially less viscous after its purpose has been served in surgery, such agents being hereinafter referred to as transitional viscoelastics. Such transitional viscoelastics may then be left by the surgeon to be eliminated gradually from the surgical site by the body's natural processes without creating a dangerous IOP spike.

Transitional viscosities are known to occur in certain agents systems. In the ophthalmic field, systems are known in which a liquid forms a gel after application to the eye. For example, such gelations may be triggered by a change in pH. See, Gurney et al., "The Development and Use of In Situ Formed Gels, Triggered by pH" *Biopharm. Ocul. Drug Delivery*, (1993) pp. 81–90. Temperature sensitive gelation systems have also been observed for certain ethyl (hydroxyethyl) cellulose ethers (EHECs) when mixed with particular ionic surfactants at appropriate concentrations. See, Carlsson et al., "Thermal Gelation of Nonionic Cellulose Ethers and Ionic Surfactants in Water" *Colloids Surf.*, volume 47, pages 147–65 (1990) and for systems of pure methylethyl cellulose, U.S. Pat. No. 5,618,800 (Kabra et al.)) Likewise, gellan gum (Gelrite®) is known to form a gel on contact with specific cations. Greaves et al., "Scintigraphic Assessment of an Ophthalmic Gelling Vehicle in Man and Rabbit," *Curr. Eye Res.*, volume 9, page 415 (1990). Gellan systems have been suggested for use as a vehicle for ophthalmic medications (Rozier et al., "Gelrite: A Novel, Ion-Activated, In Situ Gelling Polymer for Ophthalmic Vehicles. Effect on Bioavailability of Timolol," *Int. J. Pharm.*, volume 57, page 163 (1989)), and one gellan system is currently being marketed with timolol, a beta blocker, as a glaucoma medication. Carrageenans also have been suggested for use as a delivery vehicle for ophthalmic drugs. See, e.g. U.S. Pat. Nos. 5,403,841 and 5,965,152, the contents of both of which are by this reference incorporated herein. U.S. Pat. No. 5,403,841 and EP0 424043 disclose ophthalmic carrageenan compositions which transition from liquid to gel when topically applied to the eye. Finally, it is known that carrageenans can be tailored to adjust their viscosity transitions to different temperature ranges. (See, Verschueren et al. "Evaluation of various carrageenans as ophthalmic viscolysers" *STP Pharma Sci.*, volume 6, pages 203–210 (1996), and Picullel et al., "Gelling Carragreenans," *Food Polysaccharides and their Applications*, Ed: Stephen, A. M., Marcel Dekker: New York, volume 67, pages 204–44 (1995).) Kappa-carrageenans, for example, are polysaccharides which display a temperature dependent conformation wherein at high temperature the molecules exist as random coils. As the temperature is lowered, the chains associate into double helices, and, depending on the amount of potassium ($K^+$) in the solution, the double helices then self-associate into a three dimensional network. The gel formed by potassium cross-linked kappa-carrageenan is, unfortunately, very brittle, resembling the gels formed by calcium cross-linked alginate and pectin. All of these gels also exhibit syneresis, a process wherein the formation of the gel is so favored that the solvent (physiologic aqueous media here) is forced out from the gel network.

The use of a transitional viscosity viscoelastic agent as an effective surgical tool, however, especially in ophthalmic surgery, has neither been disclosed or suggested in the art. To be effective for use as an ophthalmic surgical tool, the agent, in addition to having the desired initial and transitional viscosities over the prescribed temperature range, would need to meet the following requirements: physiologically acceptable osmolarity and pH; relatively short viscosity transition time; clear (without turbidity); biocompatible; and sterilizable. The transitional viscoelastics of the present invention are believed to satisfy these requirements

SUMMARY OF THE INVENTION

The present invention is directed to improved viscous or viscoelastic agents for use in surgical procedures, especially ophthalmic surgical procedures. The improved agents of the present invention are stable, transitional viscous or viscoelastic carrageenan solutions suitable for use in ophthalmic surgery, which maintain high viscosity during the surgical procedure, but rapidly lose viscosity after the close of surgery. This rapid loss of viscosity effectively reduces or avoids the occurrence of dangerous IOP spikes, and obviates the need for active removal at the end of the surgical procedure.

Appreciating that the surface temperature of the eye tissues during surgery will approximate surgical room temperature, we have discovered stable agents that will maintain suitable viscosity at that temperature, but will rapidly lose viscosity at a slightly higher temperature (i.e., body temperature). The loss of viscosity, which occurs without the addition of a degradation agent, results from the warming of the eye back to body temperature after the surgery is complete.

DETAILED DESCRIPTION OF THE DRAWINGS

DETAILED DESCRIPTION OF THE PRESENT INVENTION

Figure 1:
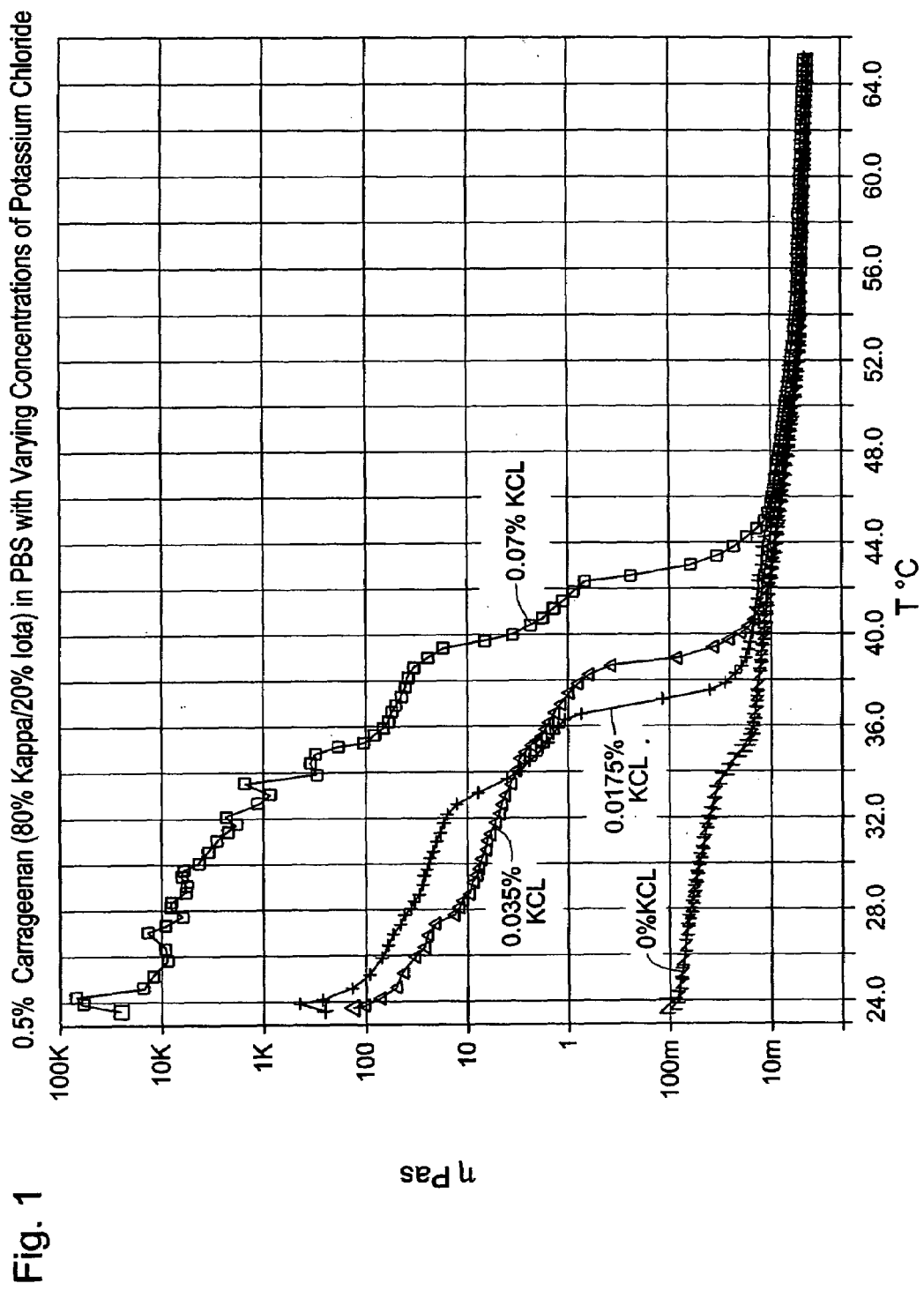
FIG. 1 is graph depicting the transitional viscosity of Carrageenan (80% kappa/20% iota) solutions of the present invention having different potassium concentrations, over a range of temperatures.

The present invention is directed to substantially stable, transitional viscoelastic materials, compositions and methods of use.

The primary use of the transitional viscoelastics is in surgical applications where the transitional viscoelastic is applied during surgery in its more viscous state and, following surgery, loses substantial viscosity in situ. A preferred use of the transitional viscoelastics is in cataract surgery, where the viscoelastic is instilled in the anterior chamber of the eye to maintain the dome and protect the exposed tissues. Following surgery, the viscoelastic is heated by the body to ambient body temperature, loses its viscosity, and is more readily removed (than non-transitional viscoelastics) by the eye's processes. The major advantage of this preferred use is the avoidance of the IOP spike present in other systems. Thus, another advantage of this use is that it allows the surgeon the traditional advantages of a viscoelastic without the disadvantage of having to aspirate the viscoelastic out of the surgical site following completion of the surgery. As stated above, such aspiration is time consuming and presents additional risk to the patient.

The transitional viscoelastics of the present invention are typically modified viscoelastics exhibiting a viscosity loss of 80% or more, when such materials undergo a temperature change of from about room temperature or surgical temperature (approximately 17–26° C.) to about body temperature (approximately 35–38° C.).

The transitional property of the present invention viscoelastics is preferably reversible. The reversible viscosity property of the preferred embodiments allows the transitional viscoelastics to be heated prior to use, e.g., heat sterilization, and then recooled for surgical application.

While bound by no theories, we postulate that the transitional viscoelastic character of the compositions of the present invention may be attributable to physical associations between relatively low molecular weight molecules resulting in a viscosity beyond what would be expected from such low molecular weight molecules at a given concentration. The viscosity of the presently claimed viscoelastic solution goes through a transition in the intraocular environment and becomes a free flowing aqueous solution. As a result, the subject viscoelastic solution can pass through the trabecular meshwork of the eye, resulting in its excretion from the anterior segment, with no or significantly reduced intraocular pressure spike.

Kappa-carrageenan is a polysaccharide which displays a temperature dependent conformation wherein at high temperature the molecules exist as random coils. As the temperature is lowered, the chains associate into double helices, and, depending on the amount of $K^+$ in the solution, the double helices then self-associate into a three dimensional network. The gel formed by potassium cross-linked kappa-carrageenan, while useful as a transitional viscoelastic, is relatively brittle and elastic compared to commercially available viscoelastics, and resembles the gels formed by calcium cross-linked alginate and pectin. All of these gels also exhibit a degree of syneresis, a process wherein the formation of the gel is so favored that the solvent (physiologic aqueous media here) is forced out from the gel network.

Surprisingly, it has been discovered that the previously described deficiencies of kappa carrageenan as a transitional viscoelastic may be overcome by blending it with one or more related polymers, preferably being pharmaceutically acceptable sulfated polysaccharides. In a preferred embodiment, kappa- and iota-carrageenan are mixed in order to reduce syneresis and the brittle nature of the kappa-carrageenan gels. The iota-carrageenan competes with the kappa-carrageenan for potassium, resulting in a more viscous and less brittle gel, while retaining a desirable transitional profile.

The kappa carrageenan and other sulfated polysaccharides of the present invention will have the weight average molecular weight ranges set forth in the following table:

| Polysaccharide | MW Range ($M_W$) | Preferred MW Range ($M_W$) |
| --- | --- | --- |
| Kappa-Carrageenan | 25–900 kDa | 50–400 kDa |
| Iota-Carrageenan | 100–3,000 kDa | 400–700 kDa |
| Chondroitin sulfate | 10–100 kDa | 20–60 kDa |
| Heparin | 2–50 kDa | 6–30 kDa |

Preferred concentrations for the kappa-carrageenan constituent, alone or mixed with another sulfated polysaccharide such as iota-carrageenan, fall in the range of 0.3 to 1.5 weight percent. Overall viscosity is directly dependent on the concentration used. The carrageenans, both kappa and iota, are commercially available from FMC Corporation, Food Ingredients Division, Rockland, Me.

For mixtures, the ratio of kappa to iota will preferably be in the range of 40 to 90% kappa to 10 to 60% iota (i.e. from about 4:6 to about 9:1) to preserve the beneficial transitional properties of the kappa constituent and the viscous gel imparting properties of the iota constituent. The potassium level should not exceed 0.10% on a weight-to-volume basis in an aqueous media based on balanced salt solution with citrate/acetate buffer or a NaCl solution with phosphate buffers. The level of potassium will modulate the transition temperature, and should be chosen so that the transition is essentially complete by 35 degrees Celsius.

The carrageenan solutions. of the present invention are autoclavable at exposure for at least 60 minutes, without appreciable reduction of their transitional viscoelastic character. Such solutions will preferably lose at least 90 percent of their pre-transition viscosity and most preferably at least 99% upon heating through the transition. As described herein, the transition temperature range will depend upon and may be controllably shifted by varying the potassium level. Preferred viscosity transition ranges, however, will be from about 17–26° C. on the lower end, to about 35–38° C. on the upper end. Most preferred is a transition temperature range from about 25° C. to about 37° C.

A unique aspect of the transitional viscoelastics of the present invention is that they possess a variable transition temperature range. The transition temperature is affected, and thus controllable, by the amount of potassium present. Furthermore, the magnitude of the transition, in terms of viscosity loss through the transition, is much greater than has been reported with hydrophobically modified materials. These materials are also steam autoclavable, and achieve useful viscosities with relatively short polysaccharide chains and concentrations of 1% or less.

The following exemplify some of the preferred kappa-/iota-carrageenan transitional viscoelastics of the present invention.

EXAMPLE 1

Solutions of 0.5 wt % carrageenan (80% kappa-/20% iota-) were made in PBS with 0% to 0.070% KCl. These samples were heated to above the transition temperature and hot filtered through a 5 micron filter. The solutions were cooled and then subjected to 50 passes through a dual hub syringe connector. Rheological data was then collected, and viscosity versus temperature data is shown in FIG. 1. The figure shows that the effect of increasing levels of potassium is to increase the pre-transition viscosity and to increase the transition temperature. Potassium ions appear to have little or no effect on the post-transition viscosity.

EXAMPLE 2

Figure 2:
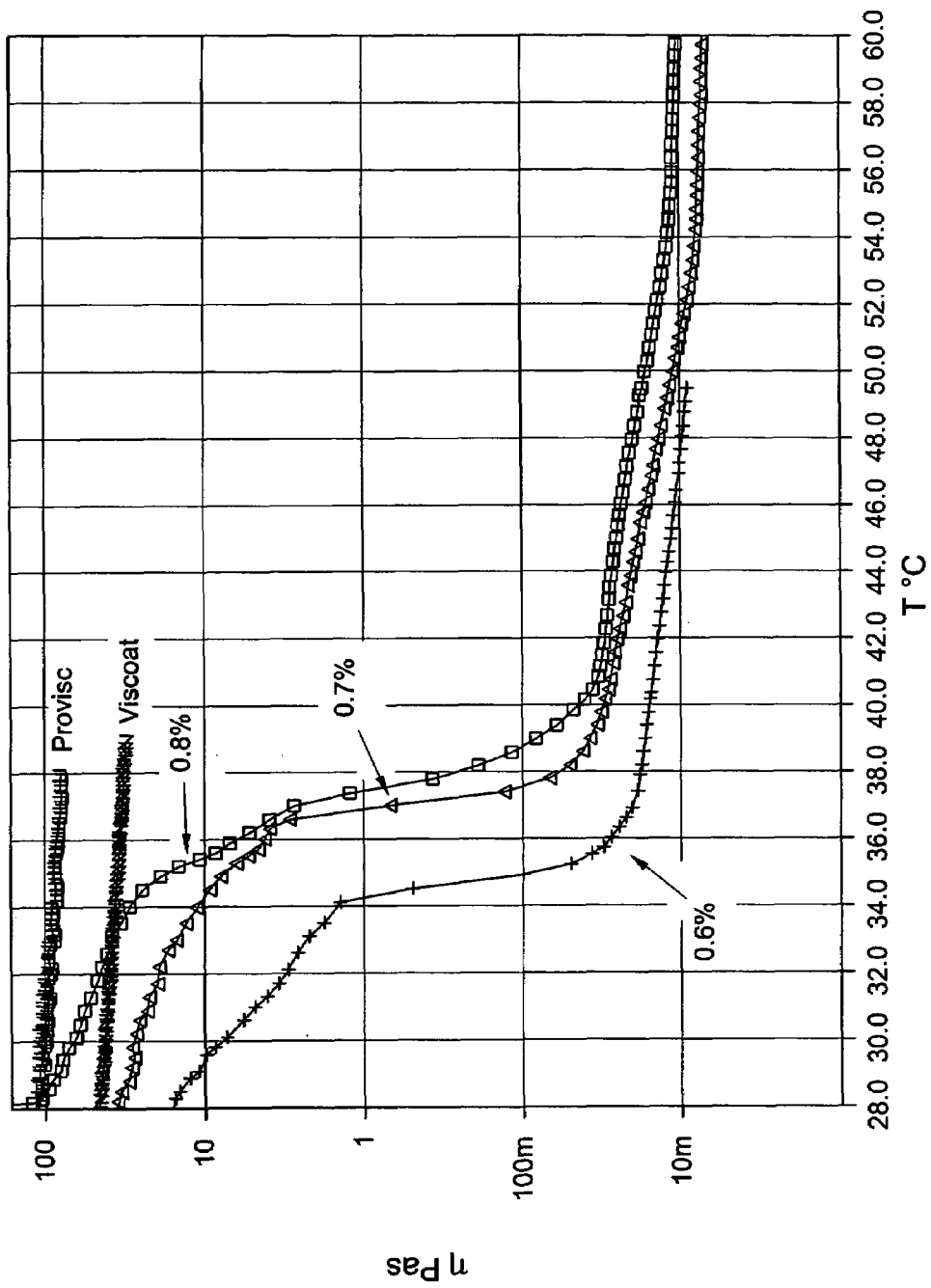
FIG. 2 is graph depicting the transitional viscosity of Carrageenan (80% kappa/20% iota) solutions of the present invention compared to commercially available viscoelastic products.

Solutions with a total of 80% kappa-carrageenan and 20% iota-carrageenan were made in phosphate buffered saline. The total solids of the solutions ranged from 0.6 wt % to 0.8 wt %. FIG. 2 shows the viscosity versus temperature Theological curves for these mixtures. The curves for PROVISC® product and for VISCOAT® product are also included as controls. The figure shows that increased solids content increases both the pre-transition viscosity and the transition temperature itself. The 0.7 wt % and the 0.8 wt % samples are viscosity matched to the VISCOAT® and PROVISC® curves at 28° C., respectively. PROVISC® and VISCOAT® lose about 33% of their viscosity over the range shown in the figure. In marked contrast, the 0.7 and 0.8% carrageenan gels lose more than 99.9% of their viscosity over the transition range from approximately 34° C. to approximately 40° C.

EXAMPLE 3

Figure 3:
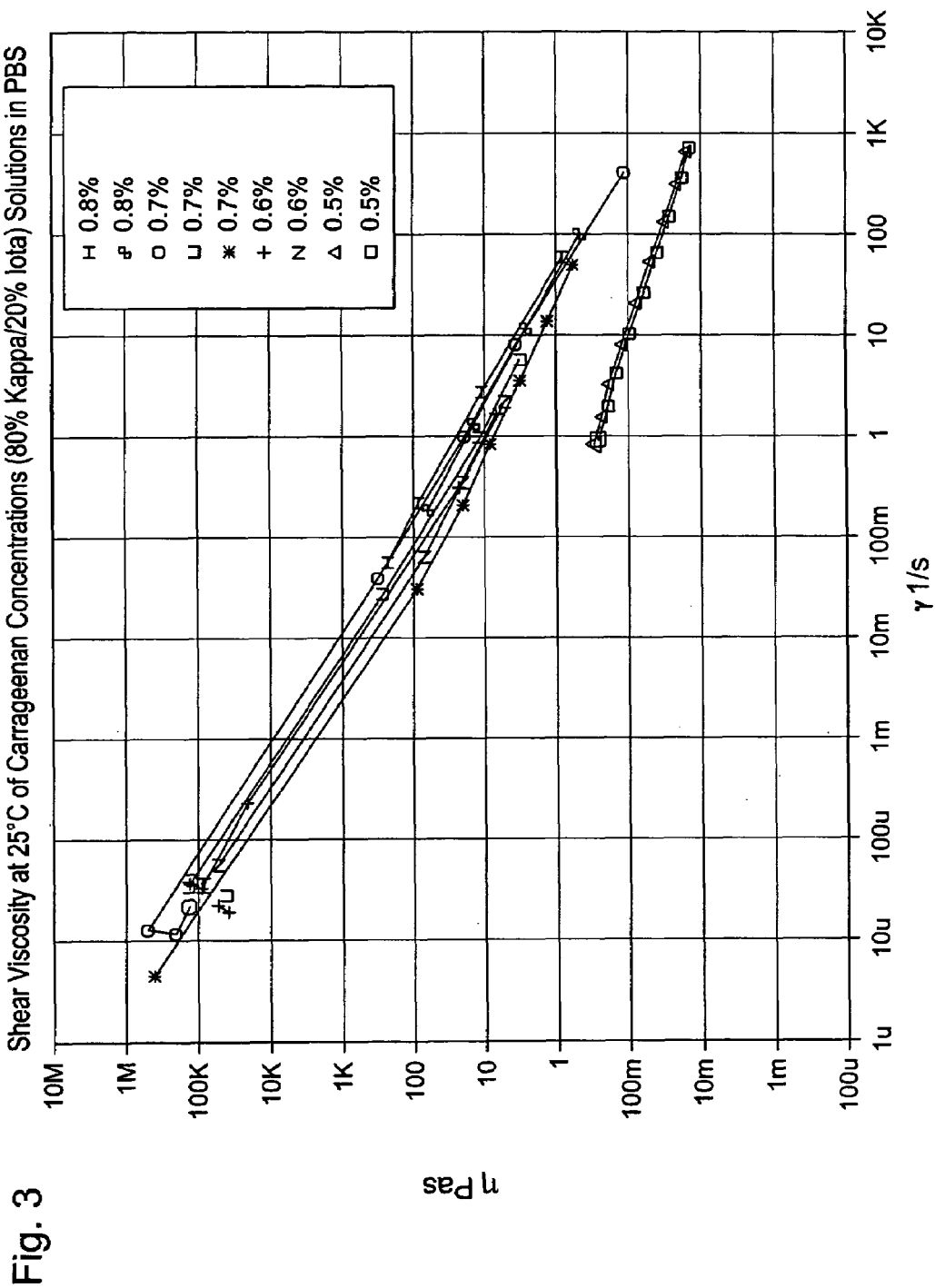
FIG. 3 is graph depicting viscosity versus shear rate for Carrageenan (80% kappa/20% iota) solutions of the present invention.

Solutions of carrageenan (80% kappa-/20% iota) were made at 0.5%, 0.6%, 0.7% and 0.8% in PBS and hot filtered and homogenized as above. FIG. 3 shows the viscosity versus shear rate dependencies for these samples. The figure shows a general increase in viscosity with increased levels of carrageenan in the solution. Interestingly, the viscosity of the 0.5% solutions are much lower than the other samples. The 0.5% samples did not gel to the extent of the higher weight percent samples.

EXAMPLE 4

Figure 4:
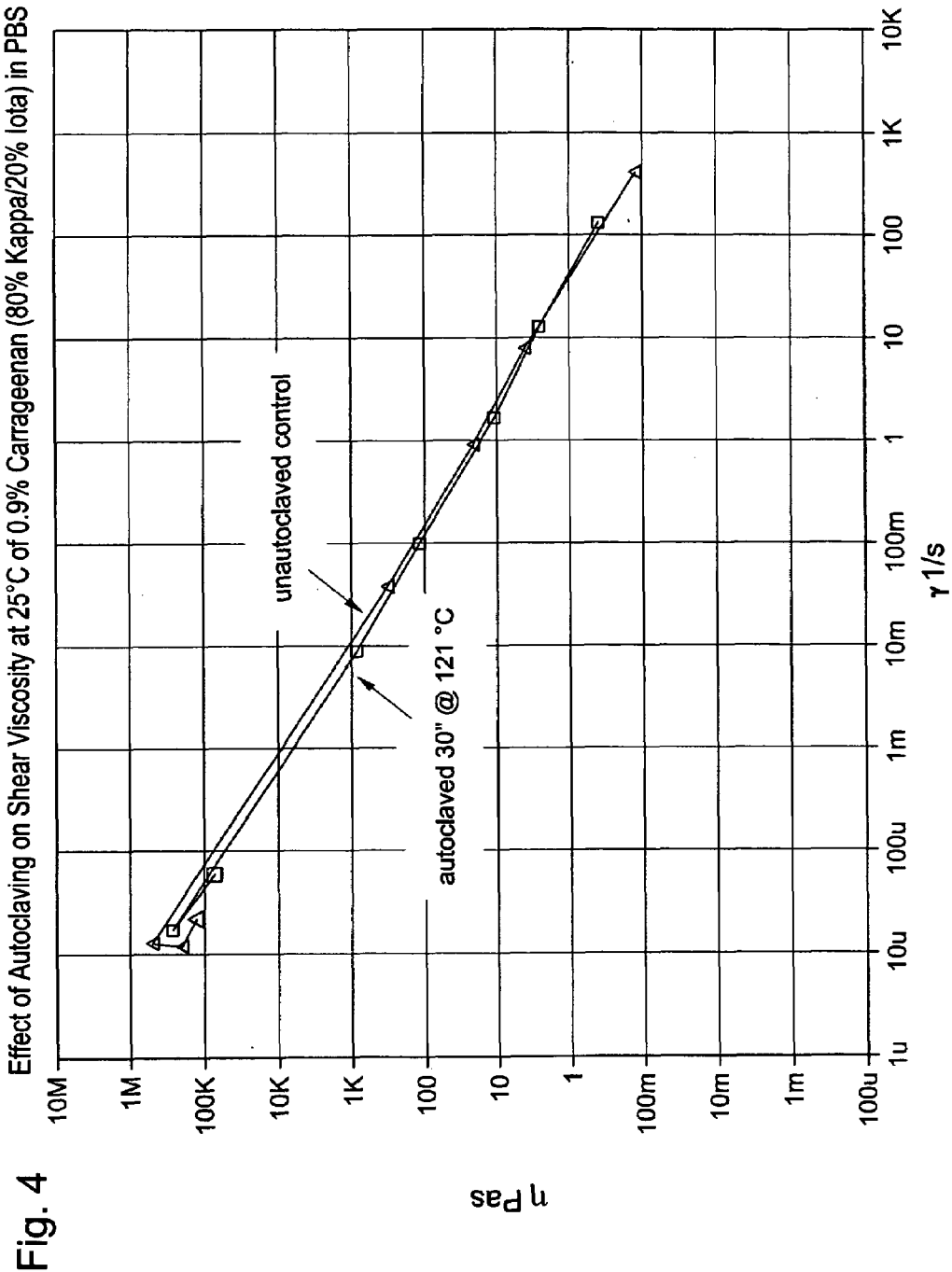
FIG. 4 is a graph depicting viscosity versus shear rate for autoclaved and unautoclaved Carrageenan (80% kappa/20% iota) solutions of the present invention.

A solution of a 0.9 wt % carrageenan (80% kappa-/20% iota-) was prepared in PBS and hot filtered and homogenized as above. This solution was split into two samples, one of which was subjected 30 minutes exposure at approximately 121° C. in a steam autoclave. FIG. 4 shows these two samples to display little variation in their rheological behavior as evidenced by the plot of viscosity versus shear rate. The curve for the autoclaved sample is generally below the control curve; however, the Theological properties of the autoclaved material are still in the very useful range.

EXAMPLE 5

Figure 5:
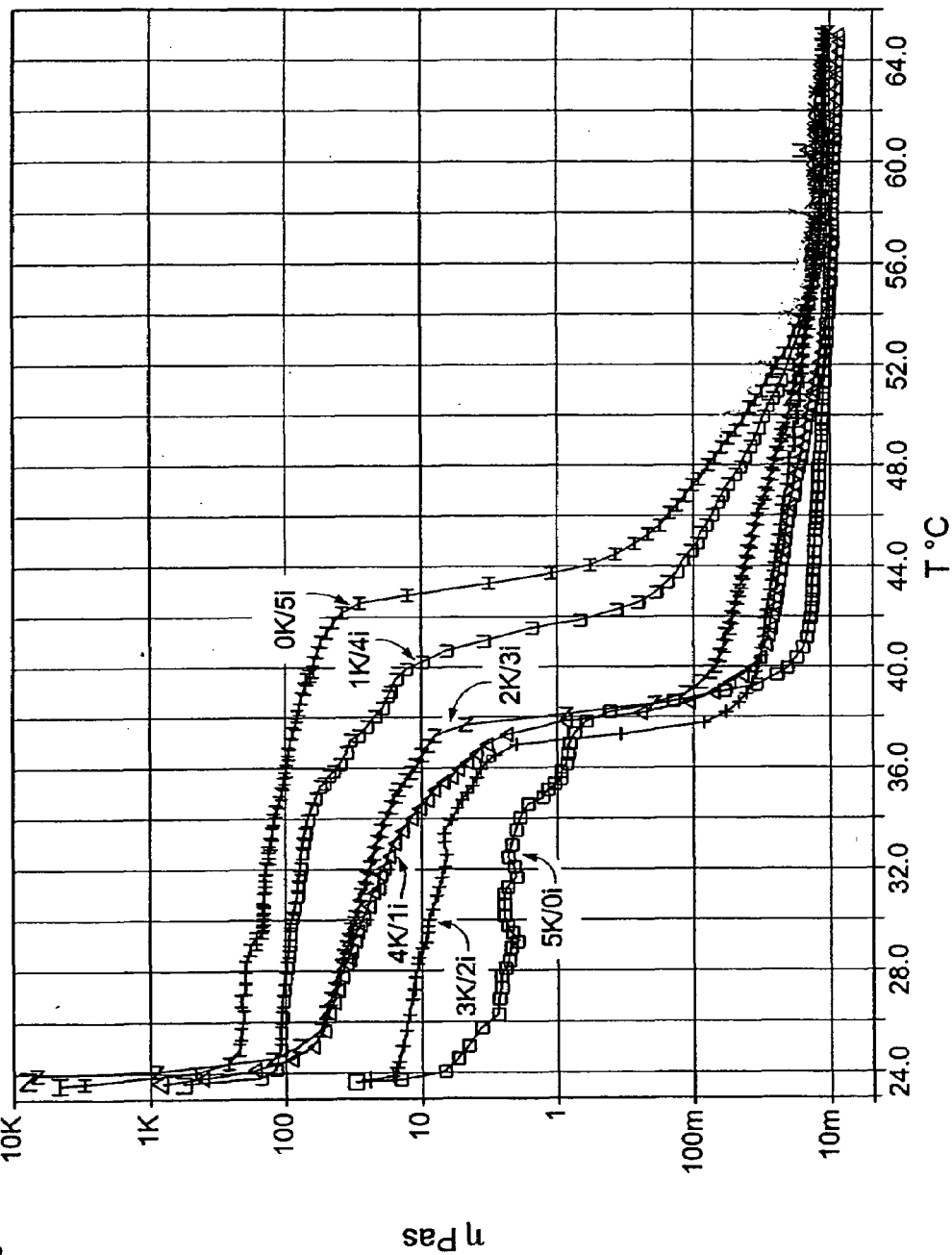
FIG. 5 is a graph depicting viscosity versus temperature for 0.8% Carrageenan solutions of the present invention with variable kappa/iota ratios.

Solutions with a total of 0.8 wt % carrageenan were made in phosphate buffered such that the ratio of kappa-carrageenan to iota-carrageenan included solutions with 0%, 20%, 40%, 60%, 80% and 100% of kappa-, with the remainder being the percent of iota-. FIG. 5 shows the viscosity versus temperature Theological data in the pre-transition, the transition, and the post-transition regions. The data support the idea that pre-transition viscosity is higher with higher percentages of iota-carrageenan. The data also support the idea that the transition temperature is lower with higher percentages of kappa-carrageenan and that the more iota- in the mixture, the more drawn out the later stages of the transition are. Based upon this figure, it is felt that too much iota raises the transition temperature and causes a tailing off of the viscosity at the end of the transition region. Thus, the iota content preferably should be less than 60 percent to preserve the transition temperature of the kappa- portion of the mixture. The iota content should further be minimized to reduce the tailing off of the viscosity at the end of the transition. However, the iota- content makes the gel more viscous and less elastic, or brittle, in nature. A balance between kappa- and iota- will depend on the total solids content used. At this total concentration, the best gels were produced at 60% kappa- and 40% iota-.

EXAMPLE 6

Figure 6:
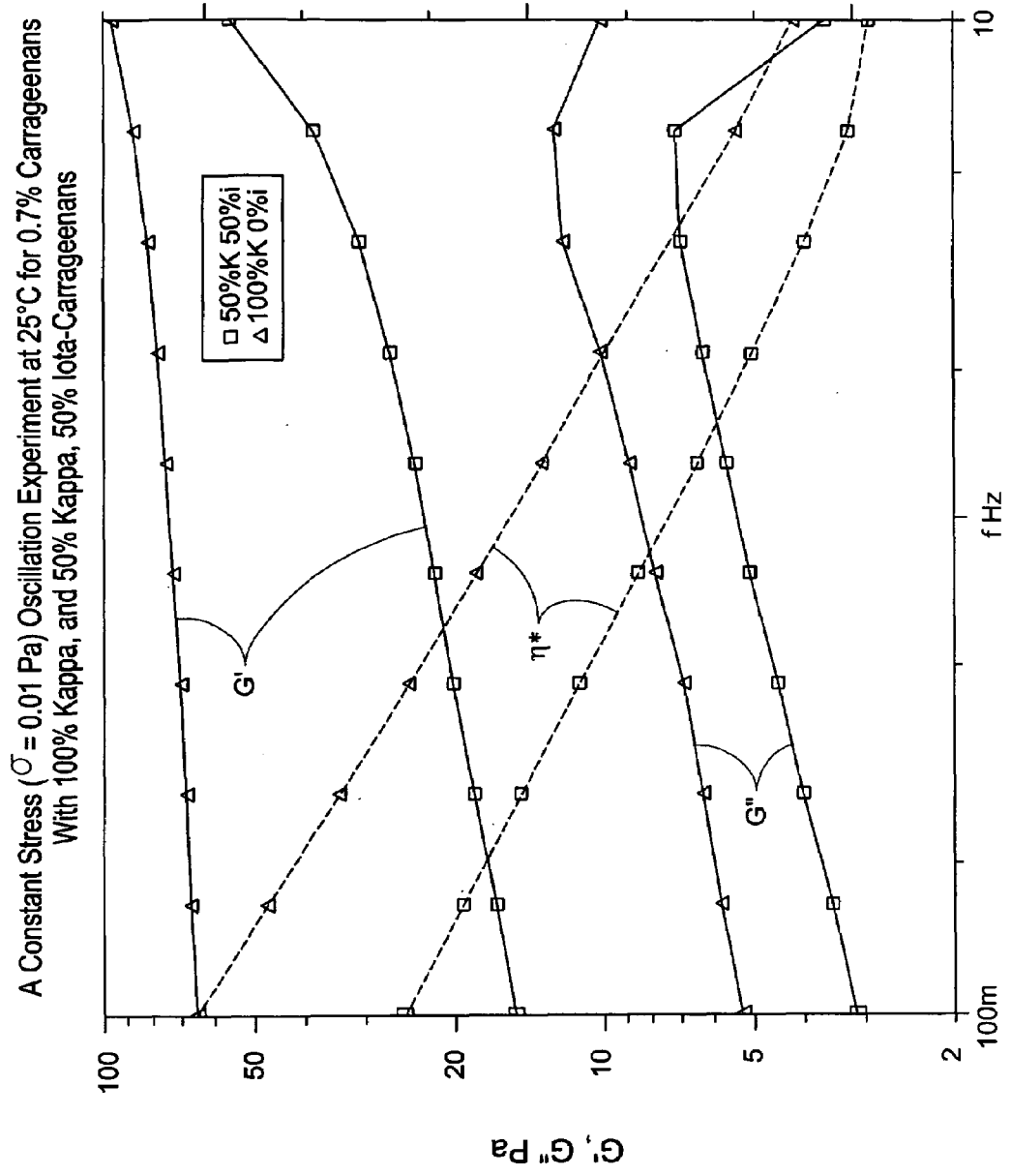
FIG. 6 is a graph depicting data from a constant stress oscillation experiment using 0.7% Carrageenan solutions of the present invention.

Samples of carrageenan at 0.7% solids were made with 50% and 100% kappa- were made in PBS and hot filtered and homogenized as above. FIG. 6 shows an oscillatory experiment performed at constant stress over a large frequence range. At a frequence of 1.29 Hz, the ratio of G" to G', in percent form, was shown to be 12.4% for the 100% kappa- and 23.4% for the 50% kappa-. This result shows that the gel with the mix of kappa- and iota- displays more viscous (G") character than the 100% kappa-.

EXAMPLE 7

Figure 7:
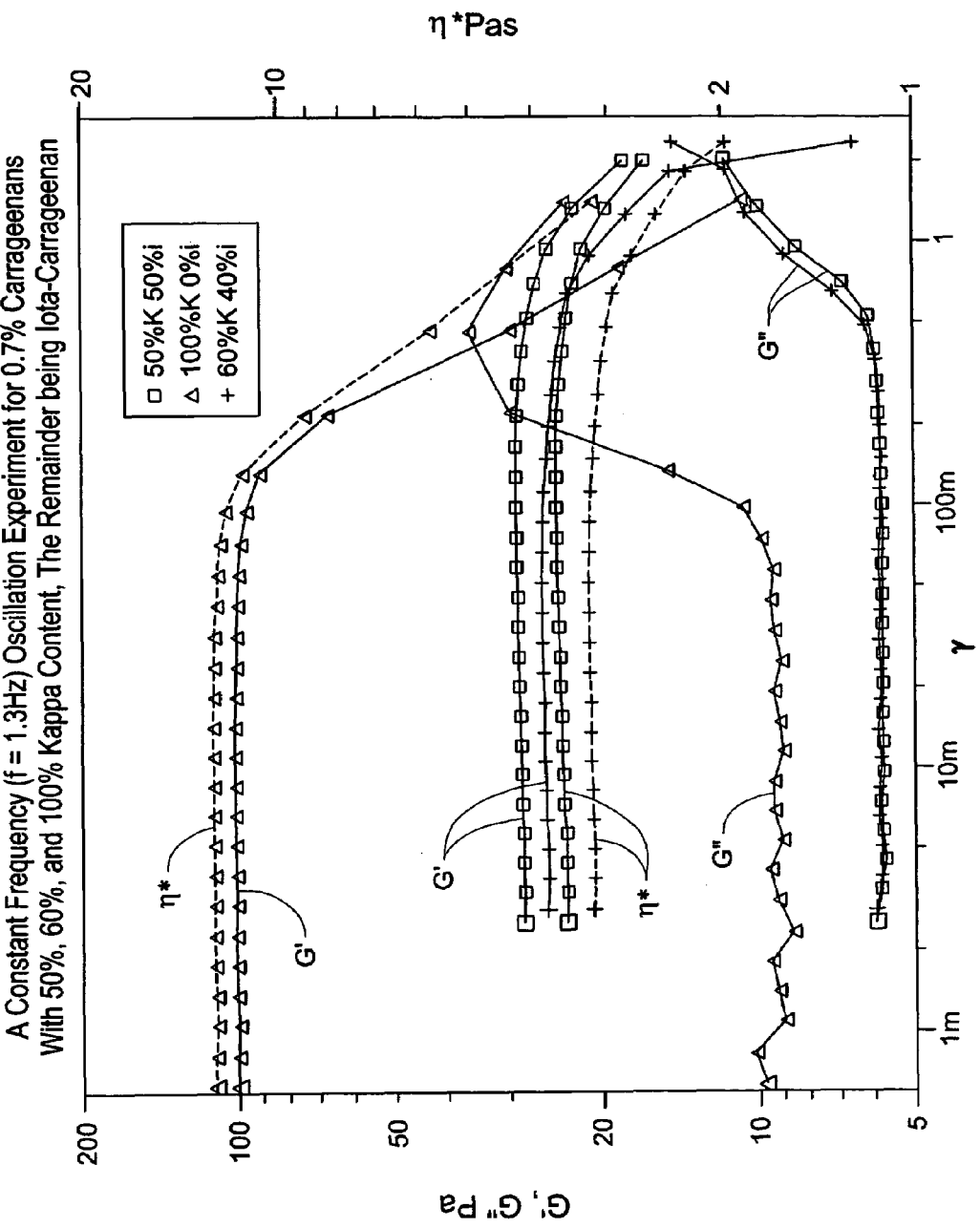
FIG. 7 is a graph depicting data from a constant frequency oscillation experiment using 0.7% Carrageenan solutions of the present invention.

Samples of carrageenan at 0.7% solids were made with 50%, 60% and 100% kappa- were made in PBS and hot filtered and homogenized as above. FIG. 7 shows an oscillatory experiment performed at constant frequency over a large strain range. At a strain of 0.01, the ratio of G" to G', in percent form, was shown to be 8.9%, 20.0%, and 22.5% for the 100%, 60% and 50% samples, respectively. This data also shows that the addition of iota- is directly related to the increase in viscous behavior and the decrease in elastic behavior.

Alternatively, the transitional viscoelastics of the present invention may comprise combinations of chondroitin sulfate and a transitional viscoelastic agent or agents.

The primary advantage of combining chondroitin sulfate with transitional viscoelastic agent lies in the ability of chondroitin sulfate to coat and protect biological tissues. In particular, the ability of chondroitin sulfate to coat the interior tissues of the eye during ocular surgery gives added protection. For example, during cataract surgery, chondroitin sulfate can coat and protect the corneal endothelium during the phacoemulsification process, which exposes the interior tissues of the eye to high ultrasound power, which can cause tissue damage. The corneal endothelium is especially important to vision since this layer of cell is vital in regulation of corneal hydration level and maintenance of the stable refractive power of the cornea. Since this tissue is not regenerated, damage to the corneal epithelial cell can cause a permanent loss in vision. As such, protection of the corneal endothelium is, therefore, also vital to a favorable outcome to cataract surgery.

Surprisingly, it has been discovered that the previously described deficiencies of kappa-carrageenan as a transitional viscoelastic may be overcome by blending it with other sulfated polysaccharides, such as chondroitin sulfate and heparin. While bound by no theories, it is believed that the sulfated polysaccharide competes with the kappa-carrageenan for potassium via its sulfate groups, resulting in a more viscous and less brittle gel. Therefore, in the case of transitional viscoelastics based on kappa-carrageenan, an additional advantage in the use of chondroitin sulfate is found beyond the ability of chondroitin sulfate to coat and protect biological and ocular tissues mentioned above.

Therefore, the preferred transitional viscoelastics of the present invention will be mixtures of chondroitin sulfate and transitional viscoelastic materials, such as, kappa-carrageenan alone or admixed with iota-carrageenan. The transitional viscoelastic agents will preferably have molecular weights from about 50,000 Daltons to about 400,000 Daltons (weight average molecular weight). Preferred concentrations for the kappa-carrageenan component, fall in the range of about 0.3 to about 1.5 weight percent. While the preferred concentration of chondroitin sulfate in these transitional viscoelastic formulations is from about 0.5 to about 4%. Overall viscosity is directly dependent on the concentration used.

The viscosities of the transitional viscoelastic formulations based on kappa-carrageenan in combination with chondroitin sulfate are also modulated by the presence of potassium ion. The potassium level should not exceed 0.10% on a weight to volume basis in an aqueous media based on balanced salt solution with citrate/acetate buffer or a NaCl solution with phosphate buffers. The level of potassium will modulate the transition temperature, and should be chosen so that the transition to minimum viscosity is essentially complete by 35° C.

Chondroitin sulfate is commercially available from Seika Gaku Corporation, Tokyo, Japan.

The effect of adding chondroitin sulfate to these kappa-carrageenan formulations, i.e. thereby increasing the overall concentration, is to reduce the elastic character as stated above. However, chondroitin sulfate will also provide small increases in pre-transition viscosity and small decreases in the transition temperature.

The following exemplify some of the preferred kappa-carrageenan/chondroitin sulfate embodiments of the present invention.

EXAMPLE 8

Figure 8:
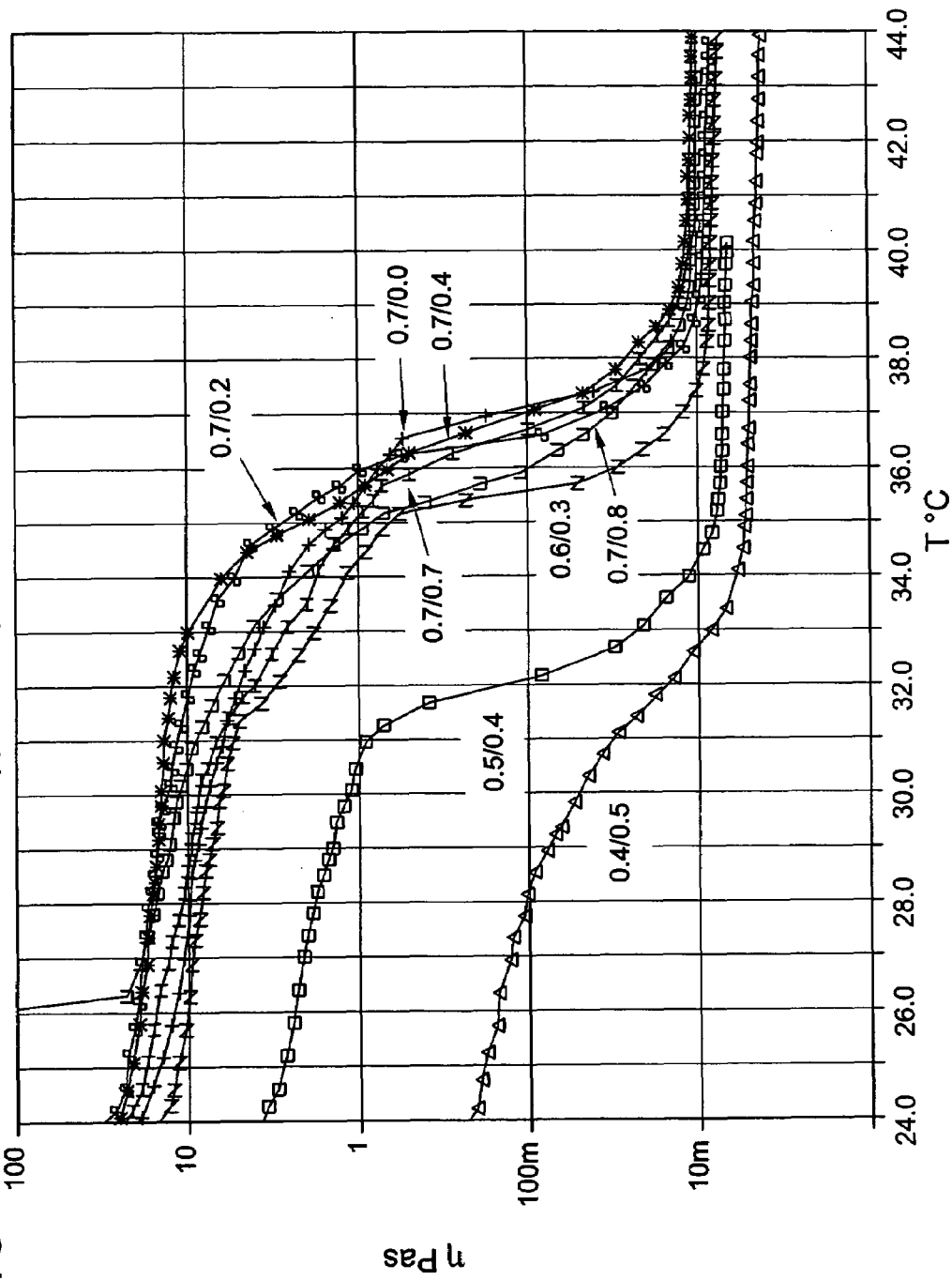
FIG. 8 is a graph depicting viscosity versus temperature for solutions of 0.7-wt% kappa-carrageenan in a phosphate buffered saline (PBS) with 0%, 0.2%, 0.4%, 0.7% and 0.8% chondroitin sulfate.

Solutions of 0.7-wt % kappa-carrageenan were made in phosphate buffered saline (PBS) with 0%, 0.2, 0.4, 0.7 and 0.8% chondroitin sulfate. These samples were heated to above the transition temperature and hot filtered through a 5-micron filter and transferred to syringes. The solutions were cooled and then subjected to 150 passes through a dual hub syringe connector. Rheological data was then collected, and viscosity versus temperature data is shown in FIG. 8. The figure shows that the effect of increasing levels of chondroitin sulfate is to essentially maintain the pre-transition viscosity and to decrease the transition temperature. Chondroitin sulfate appears to have little or no effect on the post-transition viscosity.

EXAMPLE 9

Solutions with kappa-carrageenan/chondroitin sulfate levels of 0.4%/0.5%, 0.5%/0.4%, 0.6%/0.3% and 0.7%/0.2%, such that each had a total viscoelastic content of 0.9% were made in phosphate buffered saline (PBS). These samples were heated to above the transition temperature and hot filtered through a 5-micron filter and transferred to syringes. The solutions were cooled and then subjected to 150 passes through a dual hub syringe connector. Rheological data was then collected, and viscosity versus temperature data is shown in FIG. 8. The figure shows that decreasing the ratio of kappa-carrageenan of chondroitin sulfate dramatically reduced the pre-transition viscosity and transition temperature. The 0.5% kappa-/0.4% chondroitin sulfate formulation was a viscoelastic gel rather than a brittle gel. In the absence of chondroitin sulfate, 0.4% and 0.5% kappa-carrageenan form brittle gels.

EXAMPLE 10

In order to quantify the effect of chondroitin sulfate on the viscous and elastic nature kappa-carrageenan/chondroitin sulfate viscoelastic formulations, oscillatory rheology was carried out. As demonstrated in the table below, the complex viscosity of carrageenan/chondroitin sulfate formulations (in this case having a 0.9 wt. % total solids content) decreases as the proportion of kappa-carrageenan in the formulation is decreased. Also the in the table below is a calculation for $G''/(G'+G'') \times 100\%$, where $G''$ is the viscous modulus and $G'$ is the elastic modulus. This constant frequency (1.3 Hz) experiment is carried out at 0.01 strain. The calculation shows that the viscous nature of the gel increased as the proportion of chondroitin sulfate in the mixture is increased.

TABLE

Calculation of Complex Viscosity from Oscillatory Rheology Experiment

| Formulation Composition | | Complex Viscosity: % Viscous Character = |
|---|---|---|
| % Kappa-carrageenan | % Chondroitin Sulfate | $\{G''/(G' + G'')\} \times 100$ |
| 0.4 | 0.5 | 61% |
| 0.5 | 0.4 | 33% |
| 0.6 | 0.3 | 11.5 |
| 0.7 | 0.2 | 11.0 |

The 0.7% kappa-/0.2% chondroitin and 0.6% kappa-/0.3% chondroitin formulations show about 11% viscous character; however, when the formulation contains 0.5% kappa-/0.4% chondroitin sulfate, the viscous component rises to 33%. Finally, when the formulation contains 0.4% kappa-/0.5% chondroitin sulfate, the viscous component rises to 61%.

Those skilled in the art will appreciate that the suitability of a given transitional viscoelastic for a particular step in a surgical procedure will depend upon such things as the viscoelastic's concentration, average molecular weight, viscosity, pseudoplasticity, elasticity, rigidity, adherence (coatability), cohesiveness, molecular charge, and osmolality in solution. The viscoelastic's suitability will depend further on the function(s) which the viscoelastic is expected to perform and the surgical technique being employed by the surgeon.

An appropriate buffer system (e.g., sodium phosphate, sodium acetate or sodium borate) may be added to the compositions to prevent pH drift under storage conditions.

Because all or a significant portion of the transitional viscoelastics of the present invention may be left in the eye at the close of surgery, these viscoelastics are uniquely adapted to serve the dual roles of viscosurgical tool and drug delivery device.

Ophthalmic drugs suitable for use in the compositions of the present invention include, but are not limited to: anti-glaucoma agents, such as beta-blockers including timolol, betaxolol, levobetaxolol, and carteolol; miotics including pilocarpine; carbonic anhydrase inhibitors; prostaglandin analogues including latanoprost, travoprost, and bimatoprost; seratonergics; muscarinics; dopaminergic agonists; adrenergic agonists including apraclonidine and brimonidine; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as EGF; immunosuppressant agents; and anti-allergic agents including olopatadine. The ophthalmic drug may be present in the form of a pharmaceutically acceptable salt, such as timolol maleate, brimonidine tartrate or sodium diclofenac. Compositions of the present invention may also include combinations of ophthalmic drugs, such as combinations of (i) a beta-blocker selected from the group consisting of betaxolol and timolol, and (ii) a prostaglandin analogue selected from the group consisting of latanoprost; 15-keto latanoprost; fluprostenol isopropyl ester (especially 1R-[1α(Z),2β(1E, 3R*),3α,5α]-7-[3,5-dihydroxy-2-[3-hydroxy-4-[3-(trifluoromethyl)-phenoxy]-1-butenyl]cyclopentyl]-5-heptenoic acid, 1-methylethyl ester); and isopropyl [2R(1E,3R),3S (4Z),4R]-7-[tetrahydro-2-[4-(3-chlorophenoxy)-3-hydroxy-1-butenyl]-4-hydroxy-3-furanyl]-4-heptenoate.

In the event a pharmaceutical agent is added to the transitional viscoelastics, such agents may have limited solubility in water and therefore may require a surfactant or other appropriate co-solvent in the composition. Such co-solvents typically include: polyethoxylated castor oils, Polysorbate 20, 60 and 80; Pluronic® F-68, F-84 and P-103 (BASF Corp., Parsippany N.J., U.S.A.); cyclodextrin; or other agents known to those skilled in the art. Such co-solvents are typically employed at a level of from about 0.01 to 2 wt. %. It may also be desirable to add a pharmaceutically acceptable dye to the viscoelastic to improve visualization of the viscoelastic during surgery and/or to stain ocular tissue (especially the capsular bag during capsulorhexis in cataract surgery) for improved visualization of such tissue. The use of such dyes in conventional viscoelastics is described in WO 99/58160. Preferred dyes include trypan blue, trypan red, brilliant crysyl blue, and indo cyanine green. The concentration of the dye in the viscoelastic solution will preferrably be between about 0.001 and 2 wt. %, and most preferably between about 0.01 and 0.1 wt %. However, it Will be appreciated by those skilled in the art that any such additive (pharmaceutical agents, co-solvents, or dyes) may only be employed to the extent that they do not detrimentally affect the viscoelastic properties of the compositions of the present invention.

The methods of the present invention may also involve the use of various viscoelastic agents having different adherent or cohesive properties. Those skilled in the art will recognize that the compositions of the present invention may be employed by the skilled surgeon in a variety of surgical procedures.

Given the advantages of each type of viscoelastic, the surgeon may employ is various viscoelastic compositions of the present invention in a single surgical procedure. While the use of the transitional viscoelastic of the present invention have not been disclosed for use in surgeries, U.S. Pat. No. 5,273,056 (McLaughlin et al.) discloses methods which exploit the use of compositions employing viscoelastics of varying viscoelastic properties during a given ocular surgery, the entire contents of which are incorporated herein by reference.

For example,. for portions of surgical procedures involving phacoemulsification and/or irrigation/aspiration, e.g., cataract surgery, it is generally preferable to use a viscoelastic agent that possesses relatively greater adherent properties and relatively lesser cohesive properties. Such viscoelastic agents are referred to herein as "adherent" agents. The cohesiveness of a viscoelastic agent in solution is thought to be dependent, at least in part, on the average molecular weight of that agent. At a given concentration, the greater the molecular weight, the greater the cohesiveness. Those portions of surgical procedures involving manipulation of delicate tissue are generally better served by viscoelastic agents that possess relatively greater cohesive properties and relatively lesser adherent properties. Such agents are referred to herein as "cohesive" agents. For cohesive agents such as these, which are being employed primarily for tissue manipulation or maintenance purposes as opposed to protective purposes, a functionally desirable viscosity will be a viscosity sufficient to permit the skilled surgeon to use such agent as a soft tool to manipulate or support the tissue of concern during the surgical step(s) being performed.

For other viscoelastic agents, which are being employed primarily for protective purposes ("adherent" agents) as opposed to tissue manipulation purposes, a functionally desirable viscosity will be a viscosity sufficient to permit a protective layer of such agent to remain on the tissue or cells of concern during the surgical step(s) being performed. Such viscosity will typically be from about 3,000 cps to about 60,000 cps (at shear rate of 2 $sec^{-1}$ and 25° C.), and preferably will be about 40,000 cps. Such adherent agents are capable of providing the protective function previously discussed, yet are not prone to inadvertent removal, which could jeopardize the delicate tissue being protected. Unfortunately, this same characteristic makes aspiration of such adherent viscoelastics at the end of surgery (as recommended for all such commercially available products in cataract surgery), problematic for surgeons, and subjects the coated tissues to trauma during the removal procedure. A significant advantage of the transitional viscoelastics of the present invention is that they may be left in the surgical site at the close of surgery thereby avoiding unnecessary trauma to the affected soft tissues.

Preferred methods of the present invention will employ the use of multiple viscoelastics in a given surgical procedure, wherein at least one of such viscoelastics is a transitional viscoelastic. In a most preferred embodiment of the invention, a transitional viscoelastic possessing superior adherent properties is used in cataract surgery, at the close of which some or all of it is left in situ and causes little or no IOP spike.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A transitional viscoelastic composition for use in surgery, comprising a sterile, non-inflammatory, aqueous solution comprising kappa-carrageenan, potassium, and a second sulfated polysaccharide, such solution having a viscosity transition temperature range from 17–26° C. to 35–38° C., wherein such solution exhibits a loss of viscosity of at least 80% upon heating through such viscosity transition temperature range.

2. The composition of claim 1, wherein the viscosity transition temperature range is from about 25° C. to about 37° C., and wherein the second sulfated polysaccharide is selected from the group consisting of: chondroitin sulfate, heparin, and combinations thereof.

3. The composition of claim 2, wherein the second sulfated polysaccharide is chondroitin sulfate and the weight ratio of the kappa-carrageenan to the chondroitin sulfate is from about 4:5 to about 7:2.

4. The composition of claim 3, wherein the combined concentration of the kappa-carrageenan and the chondroitin sulfate is from about 0.9 to about 1.5 wt %.

5. A transitional viscoelastic composition for delivering an ophthalmic drug to an affected eye, comprising the ophthalmic drug in a sterile, aqueous solution comprising kappa-carrageenan, potassium, and a second sulfated polysaccharide, such solution having a viscosity transition temperature range from 17–26° C. to 35–38° C., wherein such solution exhibits a loss of viscosity of at least 80% upon warming through such viscosity transition temperature range.

6. The composition of claim 5, wherein the viscosity transition temperature range is from about 25 to about 37° C. and wherein the ophthalmic drug is selected from the group consisting of: anti-glaucoma agents; anti-infective agents; steroidal and non-steroidal anti-inflammatory agents;

growth factors; immunosuppressant agents; anti-allergy agents, and combinations thereof.

7. A method of protecting, manipulating or stabilizing tissue in an eye during surgery thereon, comprising instilling in the eye a transitional viscoelastic composition comprising a sterile, non-inflammatory, aqueous solution comprising kappa-carrageenan, potassium, and a second sulfated polysaccharide, such solution having a viscosity transition temperature range from 17–26° C. to 35–38° C., wherein such solution exhibits a loss of viscosity of at least 80% upon warming through such viscosity transition temperature range.

8. The method of claim 7, further comprising the step of allowing a protecting or stabilizing effective amount of the transitional viscoelastic to remain in the eye at the close of the surgery.

9. The method of claim 7, wherein the second sulfated polysaccharide is selected from the group consisting of: iota-carrageenan, chondroitin sulfate, heparin, and combinations thereof.

10. The method of claim 9 wherein the second sulfated polysaccharide is iota-carrageenan and the weight ratio of the kappa-carrageenan to the iota-carrageenan and is from about 2:3 to about 9:1.

11. The method of claim 10, wherein the weight ratio of kappa-carrageenan to iota-carrageenan is about 3:2.

12. The method of claim 11, wherein the combined concentration of the kappa-carrageenan and the iota-carrageenan is about 0.8 wt %.

13. The method of claim 9, wherein the second sulfated polysaccharide is chondroitin sulfate and the weight ratio of kappa-carrageenan to chondroitin sulfate is from about 4:5 to about 7:2.

14. The method of claim 13, wherein the combined concentration of the kappa-carrageenan and the chondroitin sulfate is from about 0.9 to about 1.5 wt %.

15. The method of claim 7, wherein the surgery is cataract surgery.

* * * * *